United States Patent
Giese et al.

(10) Patent No.: US 9,664,684 B2
(45) Date of Patent: May 30, 2017

(54) METHODS OF TREATING CANCER USING CHEMOVIROTHERAPY

(75) Inventors: Nathalia Giese, Schriesheim (DE); Jens Werner, Dossenheim (DE); Markus Buechler, Heidelberg (DE); Thomas Giese, Schriesheim (DE); Laurent Daeffler, Heidelberg (DE); Celina Czeipluch, Heidelberg (DE); Jean Rommelaere, Heidelberg (DE); Zahari Raykov, Heidelberg (DE)

(73) Assignees: Deutsches Krebsforschungszentrum, Heidelberg (DE); Ruprecht-Karls-Universitaet Heidelberg, Heidelberg (DE); Universitaetsklinikum Heidelberg, Heidelberg (DE)

(*) Notice: Subject to any disclaimer, the term of this patent is extended or adjusted under 35 U.S.C. 154(b) by 136 days.

(21) Appl. No.: 13/643,962

(22) PCT Filed: Apr. 29, 2011

(86) PCT No.: PCT/EP2011/002154
§ 371 (c)(1),
(2), (4) Date: Jan. 3, 2013

(87) PCT Pub. No.: WO2011/134670
PCT Pub. Date: Nov. 3, 2011

(65) Prior Publication Data
US 2013/0101989 A1    Apr. 25, 2013

(30) Foreign Application Priority Data
Apr. 30, 2010  (EP) .................... 10004592

(51) Int. Cl.
*G01N 33/68* (2006.01)
*G01N 33/574* (2006.01)

(52) U.S. Cl.
CPC ....... *G01N 33/68* (2013.01); *G01N 33/57484* (2013.01)

(58) Field of Classification Search
CPC ............ C12Q 1/6886; C12Q 2600/158; G01N 2800/52
See application file for complete search history.

(56) References Cited

U.S. PATENT DOCUMENTS

| | | | |
|---|---|---|---|
| 2004/0091458 A1* | 5/2004 | Morris et al. | 424/93.2 |
| 2009/0191540 A1* | 7/2009 | Hansen et al. | 435/5 |
| 2010/0111874 A1* | 5/2010 | Liu et al. | 424/9.2 |

FOREIGN PATENT DOCUMENTS

| | | | | |
|---|---|---|---|---|
| DE | EP2082745 | * | 7/2009 | ............ A61K 35/76 |
| JP | 2007-106716 A | | 4/2007 | |
| WO | WO 2006/004907 A2 | | 1/2006 | |

OTHER PUBLICATIONS

Angelova et al. Improvement of gemcitabine-based therapy of pancreatic carcinoma by means of oncolytic parvovirus H-1PV. Clin Cancer Res. Jan. 15, 2009;15(2):511-9.*

Borkamo et al., "cDNA microarray analysis of serially sampled cervical cancer specimens from patients treated with thermochemoradiotherapy", Int. J. Radiation Oncology Biol. Phys., 2009, vol. 75, No. 5, pp. 1562-1569 (eight (8) sheets).

Tsai et al., "Gene expression profiling of breast, prostate, and glioma cells following single versus fractionated doses of radiation", Cancer Res., Apr. 15, 2007, vol. 67, No. 8, pp. 3845-3852 (eight (8) sheets).

International Search Report dated Nov. 18, 2011 (three (3) pages).
Japanese Office Action dated May 2, 2014 (four (4) pages).

* cited by examiner

*Primary Examiner* — Michelle S Horning
(74) *Attorney, Agent, or Firm* — Crowell & Moring LLP

(57) ABSTRACT

Described is a diagnostic method for predicting the response of a patient to chemovirotherapy or radiovirotherapy, comprising exposing primary tumor cells from a patient, e.g., tumor cells obtained from a brain tumor or pancreatic cancer, to (i) a parvovirus and/or (ii) a chemotherapeutic agent or radiotherapy, and determining the reduction of the expression or concentration of ISG15.

14 Claims, 5 Drawing Sheets

METHODS OF TREATING CANCER USING CHEMOVIROTHERAPY

The present invention relates to a diagnostic method for predicting the response of a patient to chemovirotherapy or radiotherapy, comprising exposing primary tumor cells from a patient to a (a) parvovirus and/or (b) a chemotherapeutic agent or radiotherapy, and determining the reduction of the expression or concentration of ISG15 (interferon stimulated gene).

Cancer is the second leading cause of death in the United States after cardiovascular disease. One in three Americans will develop cancer in his or her lifetime, and one of every four Americans will die of cancer. Malignant human gliomas account for the largest number of human malignant brain tumors. So far, the treatment of gliomas includes neurosurgical techniques (resection or stereotactic procedures), radiation therapy and chemotherapy. However, despite these therapies gliomas are considered as incurable as they fail to respond to ionizing radiation, chemotherapy and surgical resection. In other words, with these therapies only a very limited prolongation of lifespan of patients can be achieved, i.e. despite these therapies, the average life span after diagnosis is merely 12 to 16 months.

Pancreatic cancer is a malignant neoplasm of the pancreas. Each year in the United States, about 43,000 individuals are diagnosed with this condition and about 35,000 die from the disease. The prognosis is relatively poor but has improved; the three-year survival rate is now about thirty percent, but less than 5 percent of those diagnosed are still alive five years after diagnosis. Complete remission is still rather rare.

Biotherapeutics and especially oncolytic viruses have already been applied in combination with chemotherapy for the treatment of different types of cancer including PDAC (cancer of pancreatic duct) (Kasuya et al., Cancer Gene Ther. 2005; 12: 725-36). However, the use of viruses as sensitizing agents and the problem of predicting patient responsiveness to chemovirotherapy were not successfully addressed until now. In fact, previous in vitro and in vivo studies (Angelova et al., Clin Cancer Res. 2009; 15: 511-9) showed that, e.g., pancreatic tumor cells differ in their responsiveness to treatment with parvovirus (H1-PV) and also to diverse combinations of H1-PV with the standard chemotherapeutic gemcitabine. Unfortunately, molecular markers predictive for response are missing. The potential efficacy is extrapolated from the 'trial-and-error' experiments in animal models. Since it is impossible to stratify patients into groups according to the potential responsiveness, possibly effective protocols fail if applied to the wrong target group—which may profit from different application regimen.

In summary, inability to reliably predict the success of a certain combinatorial treatment, e.g. to select potentially responding patients, is a major obstacle for clinical application of chemovirotherapy or radiovirotherapy.

Thus, the technical problem underlying the present invention is to provide a diagnostic method for predicting the response of a tumor patient to chemovirotherapy or radiotherapy.

The solution to said technical problem is achieved by providing the embodiments characterized in the claims. A novel chemovirotherapeutic protocol and a test allowing individual adjustment of doses and timing prior to initiation of the treatment thus boosting the success rates of applied therapy was developed. It was found that H1-PV infection reduces ISG15 levels and thereby sensitises cancer cells for chemotherapy (e.g., with gemcitabine). Thus, measurement of ISG15 expression in primary tumor cells exposed to different doses of H1-PV and gemcitabine over varying time periods allows to predict the response to potential therapy and to adjust individual doses of parvovirus (e.g., H1-PV) necessary for effective viro-sensitization (that is resensitising cells towards chemotherapy following H1-PV infection). The experiments resulting in the present invention revealed that infection with H1-PV reduces the expression levels of ISG15 in a subset of human pancreatic cells. Thus the ability of H1-PV to down-regulate ISG15 can be used (i) to design an individual treatment protocol first using H1-PV for sensitization of patients to consequently applied gemcitabine (or other chemotherapeutics) and (ii) to generate a screening tool which can predict potential response of patient derived primary tumor cells to this particular approach prior to the initiation of the treatment. This approach can be expanded to radiovirotherapy since the IFN-related DNA damage resistance has been reported to relate to both chemo- and radioresistance (1-3). Benefits to patients and therapy-financing agencies are apparent, i.e., the approach of the present invention significantly improves the objective responses, allows individualized therapy, and is cost saving.

Figure 1:
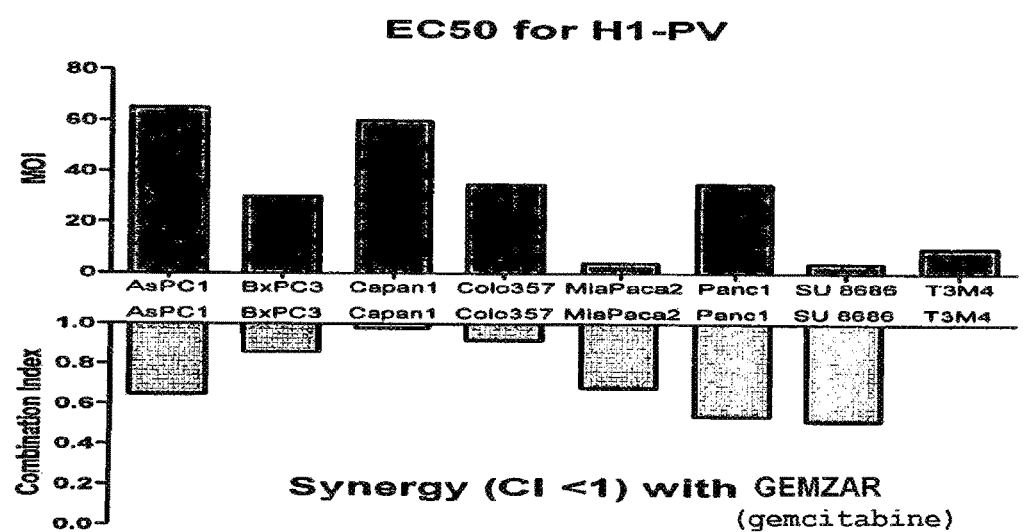
FIG. 1: Synergy of the combined treatment with H1-PV and GEMZAR (gemcitabine)

Thus, the present invention relates to a diagnostic method for predicting the response of a patient to chemovirotherapy or radiovirotherapy, comprising (a) exposing primary tumor cells of a tumor sample obtained from a patient to different doses of (i) a parvovirus and/or (ii) a chemotherapeutic agent or radiotherapy; and (b) determining the reduction of the expression or concentration of ISG15 over varying time periods.

Thus, the ISG15 expression in primary tumor cells exposed to different doses of, e.g., H1-PV and gemcitabine over varying time periods allows to predict the response to potential therapy and to adjust individual doses of parvovirus In an alternative embodiment, the present invention relates to a method of selecting a therapy modality for a patient afflicted with a tumor, comprising (a) exposing primary tumor cells of a tumor sample obtained from a patient to different doses of (i) a parvovirus and/or (ii) a chemotherapeutic agent or radiotherapy; and (b) determining the reduction of the expression or concentration of ISG15 over varying time periods.

Based on the results of step (b) the response of a patient to chemovirotherapy/radiotherapy can be predicted and the most suitable therapy modality selected, i.e., both a cut-off value can be established and a test selects suitable patients and adjust an appropriate dose for these patients.

The terms "chemovirotherapy" and "radiovirotherapys" as used herein, refer to a combination of (parvo)virotherapy with chemotherapy and radiotherapy, respectively. The parvovirus can be administered prior to, simultaneously with or after administration of the chemotherapeutic agent or radiotherapy. Preferably, the parvovirus is administered prior to the chemotherapeutic agent or radiotherapy.

The term "tumor sample" as used herein, refers to a sample obtained from a patient. The tumor sample can be obtained from the patient by routine measures known to the person skilled in the art, i.e., biopsy (taken by aspiration or punctuation, excision or by any other surgical method leading to biopsy or resected cellular material). For those areas not easily reached via an open biopsy, a surgeon can, through a small hole made in the skull, use stereotaxic instrumentation to obtain a "closed" biopsy. Stereotaxic instrumentation allows the surgeon to precisely position a biopsy probe in three-dimensional space to allow access almost anywhere in the brain. Therefore, it is possible to obtain tissue for the diagnostic method of the present invention.

The term "tumor" is not limited to any stage, grade, histomorphological feature, invasiveness, agressivity or malignancy of an affected tissue or cell aggregation. In particular stage 0 cancer, stage I cancer, stage II cancer, stage III cancer, stage IV cancer, grade I cancer, grade II cancer, grade III cancer, malignant cancer, primary carcinomas, and all other types of cancers, malignancies etc. are included.

The term "parvovirus" as used herein comprises wild-type or modified replication-competent derivatives thereof, as well as related viruses or vectors based on such viruses or derivatives. Suitable parvoviruses, derivatives, etc. as well as cells which can be used for actively producing said parvoviruses and which are useful for therapy, are readily determinable within the skill of the art based on the disclosure herein, without undue empirical effort. Examples of parvoviruses useful in the present invention include parvovirus H1 (H1-PV) or a related parvovirus such as LuIII, Mouse minute virus (MMV), Mouse parvovirus (MPV), Rat minute virus (RMV), Rat parvovirus (RPV) or Rat virus (RV).

ISG15 is an IFN-alpha/beta-induced ubiquitin-like protein that is conjugated to a wide array of cellular proteins through the sequential action of three conjugation enzymes that are also induced by IFN-alpha/beta. The amino acid sequence of the protein as well as the nucleotide sequence of the gene encoding ISG15 are described in (4) and (5). Thus, the person skilled in the art can generate probes suitable for determining the expression and/or concentration of ISG15 according to standard methods. The person skilled in the art also knows routine methods for cultivating or maintaining primary tumor cells and incubating these cells with the parvovirus and/or chemotherapeutic agent.

The methods of the invention can be applied to any tumor. However, preferred tumors are brain tumor and pancreatic cancer.

Patients treatable by the combination of agents according to the invention include humans as well as non-human animals. Examples of the latter include, without limitation, animals such as cows, sheep, pigs, horses, dogs, and cats.

Chemotherapeutic agents useful for the purposes of the present invention include all chemical compounds that are effective in inhibiting tumor growth. The administration of chemotherapeutic agents can be accomplished in a variety of ways including systemically by the parenteral and enteral routes. Preferably, the parvovirus and the chemotherapeutic agent are administered as separate compounds. Examples of suitable chemotherapeutic agents include alkylating agents, for example, nitrogen mustards, ethyleneimine compounds and alkyl sulphonates; antimetabolites, for example, folic acid, purine or pyrimidine antagonists, mitotic inhibitors, for example, vinca alkaloids and derivatives of podophyllotoxin; cytotoxic antibiotics; compounds that damage or interfere with DNA expression; and growth factor receptor antagonists.

Particular examples of chemotherapeutic agents suitable for the combined therapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof. Particularly preferred chemotherapeutic agents are gemcitabine and temozolodine.

The expression of the gene encoding ISG15 and the concentration of the ISG15 protein can be assayed by standard methods known to the person skilled in the art. The nucleic acid sequence and derived amino acid sequence of ISG15 have been published (4). Preferred assays are based on hybridization or by PCR using appropriate probes/primer pairs, such as Northern blot analysis, reverse transcription polymerase chain reaction (RT-CR), in situ hybridization, etc.

"Primer pairs" and "probes", within the meaning of the present invention, shall have the ordinary meaning of this term which is well known to the person skilled in the art of molecular biology. In a preferred embodiment of the invention "primer pairs" and "probes" shall be understood as being polynucleotide molecules having a sequence identical, complementary, homologous, or homologous to the complement of regions of a target ISG15 protein which is to be detected. The primers/probes may be detectably labeled helpful in the detection of the protein. Preferred labels are fluorescent labels, luminescent labels, radioactive labels and dyes.

Preferably, the concentration of the ISG15 protein is determined by using an antibody that specifically binds to the ISG15 protein. Such an antibody can be generated using an ISG15 derived peptide or the entire protein as an immunogen.

The term "antibody" as used herein relates to any type of antibody known in the art. An antibody as used herein includes intact immunoglobulin molecules, as well as fragments thereof, such as Fab, F(ab)$_2$, and Fv, which are capable of binding an epitope of IDH1. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to ISG15 can be used in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

An antibody useful in the diagnostic method of the present invention can be raised according to well established methods, i.e., an ISG15 polypeptide or fragment thereof can be used to immunize a mammal, such as a mouse, rat, rabbit, guinea pig, monkey, or human, to produce polyclonal antibodies. If desired, the (poly)peptide used as an immunogen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (*bacilli* Calmette-Guerin) and *Corynebacterium parvum* are especially useful.

Monoclonal antibodies which specifically bind to ISG15 can be prepared using any technique which provides for the production of antibody molecules by continuous cell lines in culture. These techniques include, but are not limited to, the hybridoma technique, the human B cell hybridoma technique, and the EBV hybridoma technique [Kohler et al., Nature 256 (1985), 495-7).

Antibodies useful in a method of the invention can be purified by methods well known in the art. For example, antibodies can be affinity purified by passage over a column to which an ISG15 polypeptide is bound. The bound antibodies can then be eluted from the column using a buffer with a high salt concentration.

The invention is not limited to a particular immunoassay procedure, and therefore is intended to include both homogeneous and heterogeneous procedures. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In the method of the present invention which relates to the selection of a therapy modality for a patient afflicted with a tumor the term "therapy modality", inter alia, refers to a timely sequential or simultaneous administration of a parvovirus and a chemotherapeutic agent for cancer therapy. The administration of these can be performed in an adjuvant and/or neoadjuvant mode. The variation of the dose of the single agent, timeframe of application and frequency of administration within a defined therapy window depends on the reduction of the expression/level/activity of ISG15 after primary tumor cells of tumor samples obtained from a patient have been exposed to different doses of a parvovirus and/or a chemotherapeutic agent. However, the assay results obtained might even indicate that the patient may profit more from a different treatment regimen. Thus, the term "therapy modality" is not restricted to administration of a parvovirus and a chemotherapeutic agent.

The invention also provides a kit useful for carrying out a method of the invention, comprising an antibody that specifically binds to an ISG15 protein, or a probe or primer pair as described above, i.e., specifically hybridizing to the ISG15 mRNA.

The following examples illustrate the invention.

EXAMPLE 1

Infection With H1-PV Reduces the Expression Levels of ISG 15

Figure 2:
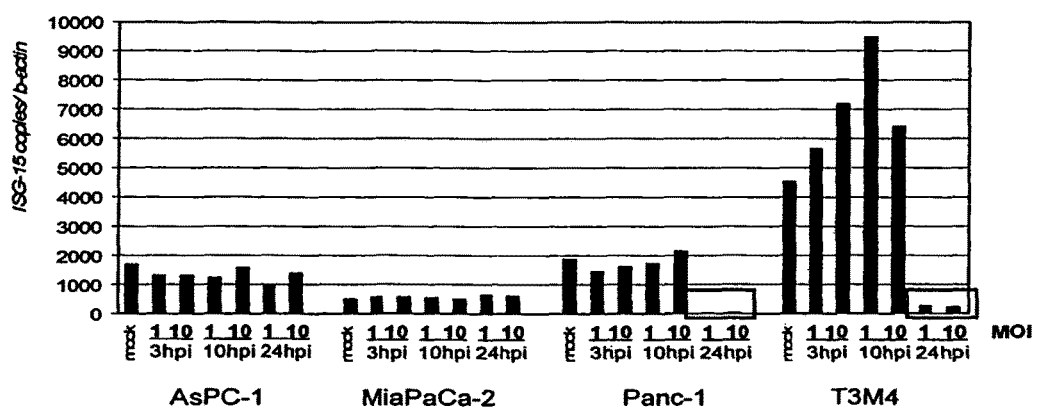
FIG. 2: Downregulation of ISG15 by H-1PV (QRT-PCR)
See Example 2 for details.
Figure 3:
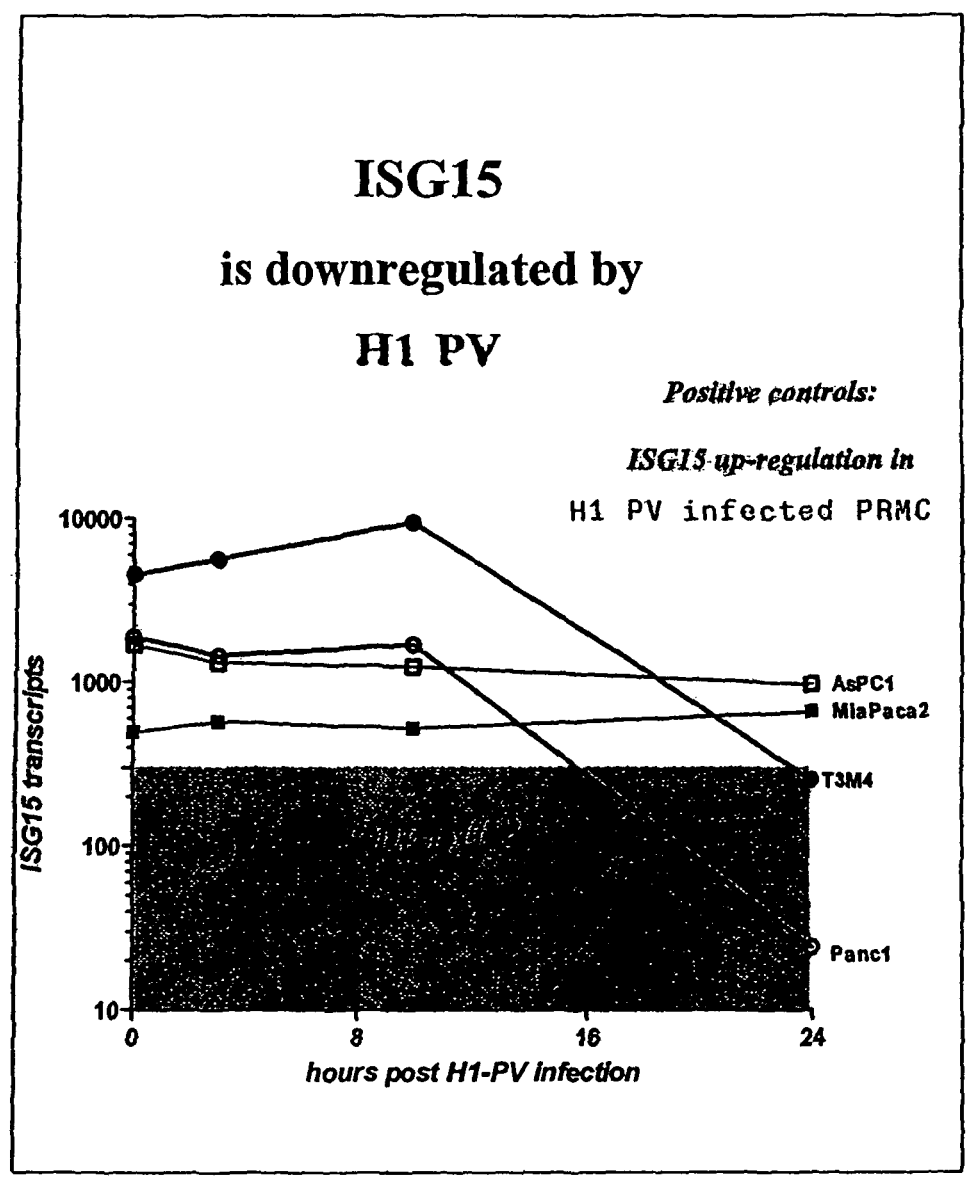
FIG. 3: Downregulation of ISG15 by H-1PV
See Example 2 for details.

Recent experiments revealed that infection with H1-PV reduces the expression levels of the ISG 15 in a subset of human pancreatic cells. AsPC1, MiaPaCa2, Panc1 and T3M4 cell lines were seeded in 24 well plates and infected with H-1PV at MOIs of 1 and 10. At 3, 10 and 24 hrs post infection (hpi) cells were harvested in 300 µl of MagNA Pure LC mRNA lysis buffer (Roche) and after purification of mRNA subjected to QRT-PCR using primers for human ISG15, β-actin and H-1PV. The ISG15 copy numbers were drastically reduced in infected T3M4 and to a lesser extent in Panc1 cells (FIGS. 2 and 3).

EXAMPLE 2

Comparison of the Protocols of Applying Either GEMZAR (Gemcitabine) or H-1PV as First Line Treatment An initial experiment was performed to compare the protocols of applying either GEMZAR (gemcitabine) or H-1PV as first line treatment with a 24 hrs difference. The above-mentioned pancreatic cell lines were plated in a 96 well plate and treated with MOIs 1 or 10 and an EC50 dose of GEMZAR (gemcitabine) using the following scheme. An MTT cytotoxicity assay was performed at 72 and 96 hrs to assess the levels of cell growth inhibition.

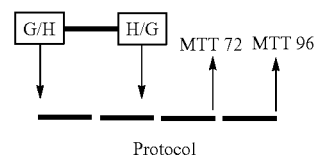

Protocol

24hrs

Figure 4:
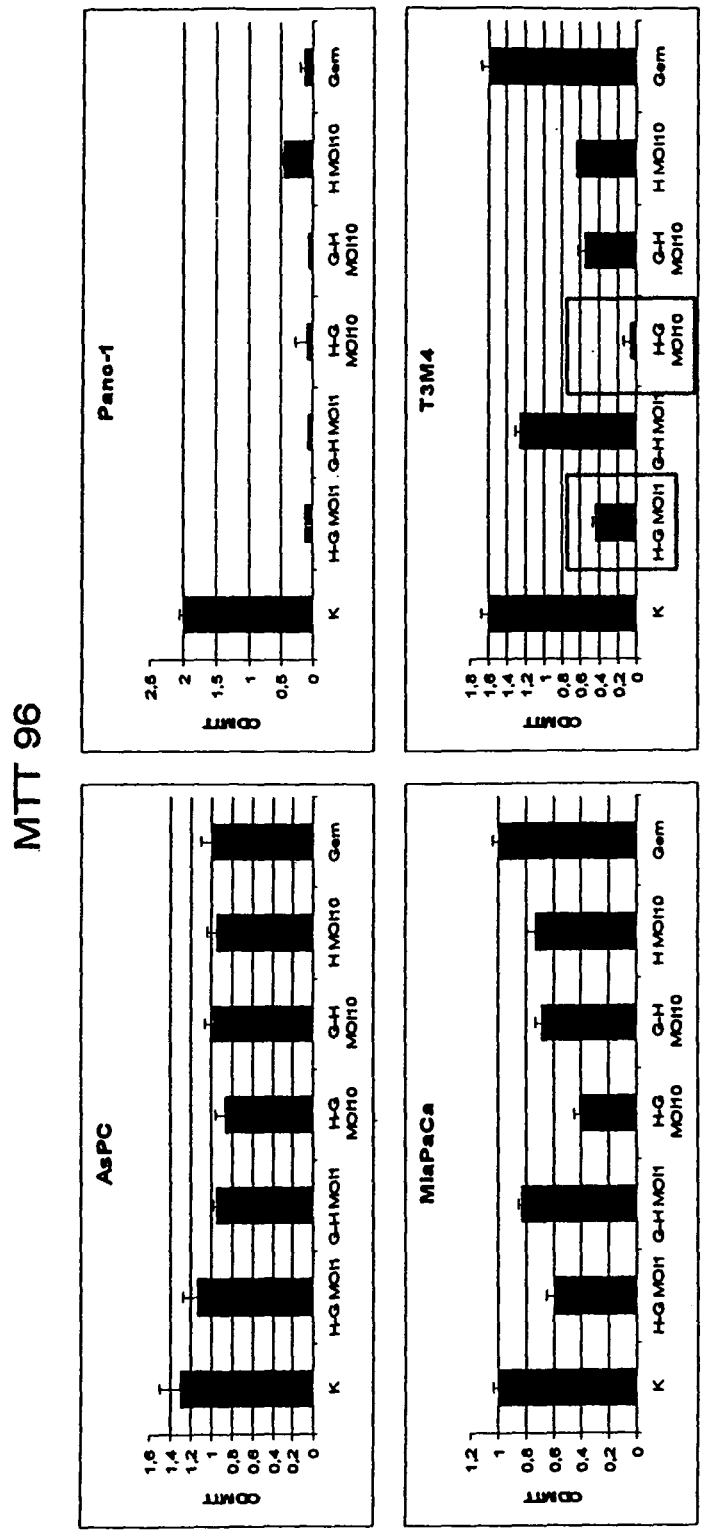
FIG. 4: Comparison of the protocols of applying either GEMZAR (gemcitabine) or H-lPV as first line treatment
See Example 2 for details.

The results of this initial experiment are shown in FIG. 4. The assumption concerning the improved effectiveness of the H/G (H-1PV-24h GEMZAR (gemcitabine); H-G MOI 1 or H-G MOI 10) compared to the G/H (GEMZAR (gemcitabine)-24h-H-1PV; G-H MOI 1 or G-H MOI 10) protocol could be confirmed in the case of T3M4 cells where the virus induces ISG15 reduction (see FIGS. 2 and 3).

EXAMPLE 3

Figure 5:
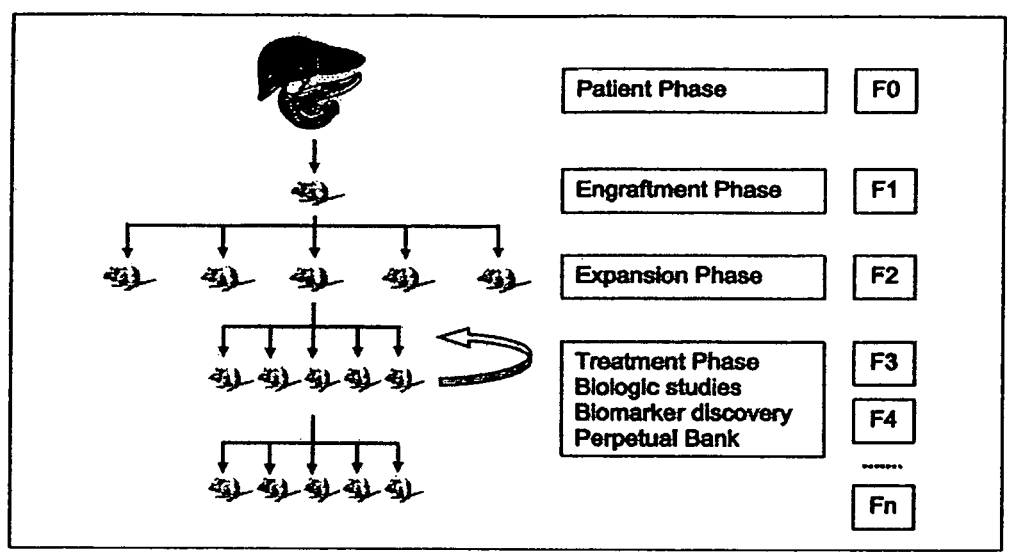
FIG. 5: Samples obtained during routine PDAC surgeries are (i) used to establish short- and long-term primary cultures, and simultaneously (ii) xenotransplanted into SCID mice and then expanded
See Example 3 for details.

Selection of Patients Potentially Responsive To the Protocol Based On Use of H-1PV As An ISG15-Dependent Gemcitabine-Sensitizer Samples obtained during routine PDAC surgeries (n=6) will be i) used to establish short- and long-term primary cultures, and will be simultaneously ii) xenotransplanted into SCID mice (F0) and future expanded (F1/F2) (see FIG. 5). The inhibitory effect of H-1PV on ISG15 expression will be tittered both in vitro using both QRT-PCRs and Western blots. Rabbit Polyclonal Antibody to human ISG15 (Axxora: Boston) will be used as the primary antibody at 1:500 dilution and in vivo. A minimal effective dose of the virus will be established. The degree of tumor cell death will serve as functional read-out.

Surgically obtained PDAC material will be used to a establish QRT- or IHC-based screening tool enabling timely selection of patients potentially responsive to the protocol based on use of H-1PV as an ISG15-dependent gemcitabine-sensitizer.

LIST OF REFERENCES

1. An interferon-related gene signature for DNA damage resistance is a predictive marker for chemotherapy and radiation for breast cancer. Weichselbaum R R, Ishwaran H, Yoon T, Nuyten D S, Baker S W, Khodarev N, Su A W, Shaikh A Y, Roach P, Kreike B, Roizman B, Bergh J, Pawitan Y, van de Vijver M J, Minn A J. Proc Natl Acad Sci USA. 2008; 105(47):18490-5.
2. Signal transducer and activator of transcription 1 regulates both cytotoxic and prosurvival functions in tumor cells. Khodarev N N, Minn A J, Efimova E V, Darga T E, Labay E, Beckett M, Mauceri H J, Roizman B, Weichselbaum R R. Cancer Res. 2007; 67(19):9214-20.
3. STAT1 is overexpressed in tumors selected for radioresistance and confers protection from radiation in transduced sensitive cells. Khodarev N N, Beckett M, Labay E, Darga T, Roizman B, Weichselbaum R R. Proc Natl Acad Sci USA. 2004; 101(6):1714-9. Epub 2004 Jan. 30.
4. Molecular characterization of the interferon-induced 15-kDa protein. Molecular cloning and nucleotide and amino acid sequence. Blomstrom D C, Fahey D, Kutny R, Korant B D, Knight E Jr. J Biol Chem. 1986; 261(19): 8811-6.
5. Production of ISG-15, an interferon-inducible protein, in human corneal cells. Taylor J L, D'Cunha J, Tom P, O'Brien W J, Borden E C. J Interferon Cytokine Res. 1996; 16(11):937-40.

The invention claimed is:
1. A method of treating cancer in a patient comprising
   (a) exposing primary tumor cells of a pancreatic tumor sample obtained from a patient to different doses of (i) parvovirus H1 and (ii) GEMZAR (gemcitabine);
   (b) determining the expression or concentration of ISG15 over varying time periods;
   (c) identifying whether the expression or concentration of ISG15 has been reduced over the varying time periods which is indicative for the patient's sensitivity to chemovirotherapy;
   (d) administering chemovirotherapy comprising parvovirus H1 and GEMZAR to a patient, wherein cancer is treated in the patient.
2. A method of treating cancer in a patient according to claim 1, wherein the cancer is a or pancreatic cancer.
3. The method claim 1, wherein the expression of ISG15 is determined on the mRNA level.
4. The method of claim 3, wherein the mRNA level is determined by a hybridization based method or by PCR.
5. The method of claim 1, wherein the concentration of ISG15 is determined using an antibody that specifically binds to ISG15.
6. The method claim 2, wherein the expression of ISG15 is determined on the mRNA level.
7. The method of claim 6, wherein the mRNA level is determined by a hybridization based method or by PCR.
8. The method of claim 2, wherein the concentration of ISG15 is determined using an antibody that specifically binds to ISG15.
9. The method of treating cancer according to claim 1, wherein the patient is a human.
10. The method of treating cancer according to claim 2, wherein the patient is a human.
11. The method of treating cancer according to claim 1, wherein administering is by a parenteral or enteral route.
12. The method of treating cancer according to claim 2, wherein administering is by a parenteral or enteral route.
13. The method of treating cancer according to claim 1, wherein parvovirus H1 and GEMZAR are administered to the patient separately.
14. The method of treating cancer according to claim 2, wherein parvovirus H1 and GEMZAR are administered to the patient separately.

* * * * *